US010416097B2

(12) United States Patent
Freeman et al.

(10) Patent No.: US 10,416,097 B2
(45) Date of Patent: Sep. 17, 2019

(54) METHOD OF SCANNING AEROFOIL BLADES

(71) Applicant: ROLLS-ROYCE plc, London (GB)

(72) Inventors: Felicity Freeman, Derby (GB); Philip E Bamforth, Loughborough (GB); Richard House, Derby (GB); Terence I Simpson, Derby (GB)

(73) Assignee: ROLLS-ROYCE plc, London (GB)

( * ) Notice: Subject to any disclaimer, the term of this patent is extended or adjusted under 35 U.S.C. 154(b) by 465 days.

(21) Appl. No.: 15/150,883

(22) Filed: May 10, 2016

(65) Prior Publication Data

US 2016/0334345 A1    Nov. 17, 2016

(30) Foreign Application Priority Data

May 12, 2015 (GB) .................................. 1508065.8

(51) Int. Cl.
*G01N 23/04* (2018.01)
*G01N 23/046* (2018.01)

(52) U.S. Cl.
CPC ..... *G01N 23/046* (2013.01); *G01N 2223/419* (2013.01); *G01N 2223/63* (2013.01)

(58) Field of Classification Search
CPC ......... G01N 2223/63; G01N 2223/419; G01N 23/046
See application file for complete search history.

(56) References Cited

U.S. PATENT DOCUMENTS 4,803,639 A * 2/1989 Steele ................... G01N 23/18
378/4
4,989,225 A * 1/1991 Gupta .................. G01N 23/046
378/10

(Continued)

FOREIGN PATENT DOCUMENTS

| CN | 101435784 | * | 5/2009 |
| CN | 101435784 A | | 5/2009 |
| EP | 2587450 A1 | | 5/2013 |

OTHER PUBLICATIONS

English translation of CN101435784.*

(Continued)

*Primary Examiner* — Dani Fox
*Assistant Examiner* — Soorena Kefayati
(74) *Attorney, Agent, or Firm* — Oliff PLC (57) ABSTRACT

A method of CT scanning a plurality of aerofoil blades that includes providing a rotatable support arranged for rotation about an axis of rotation and within an energy beam; mounting a plurality of aerofoil blades to the support in spaced-apart relationship to one another to form at least one array around the axis of rotation; and rotating the support about the axis within the beam. Each blade has an aerofoil section and is mounted to the support. The method also provides an elongate identification element on the rotatable support, the identification element being arranged such that its longitudinal axis is parallel to the axis of rotation and having a transverse cross-sectional shape along at least part of its. Each edge feature corresponds to and is directed towards a respective said blade to thereby facilitate identification of individual the blades in a CT output obtained via the method.

17 Claims, 8 Drawing Sheets

(56) References Cited

U.S. PATENT DOCUMENTS

| | | | | |
|---|---|---|---|---|
| 5,023,805 | A * | 6/1991 | Aune | B27B 1/007 378/51 |
| 5,119,408 | A * | 6/1992 | Little | G01N 23/046 378/10 |
| 5,228,071 | A * | 7/1993 | Kamata | G01N 23/046 378/20 |
| 5,319,693 | A * | 6/1994 | Eberhard | A61B 6/032 378/19 |
| 5,635,728 | A * | 6/1997 | Cantu | G01N 23/04 250/584 |
| 6,658,089 | B1 * | 12/2003 | Mohr | G01N 23/04 378/162 |
| 6,888,924 | B2 * | 5/2005 | Claus | A61B 6/583 378/163 |
| 9,121,808 | B2 * | 9/2015 | Leyte Guerrero | G01N 15/088 |
| 9,804,106 | B2 * | 10/2017 | Rothe | G01N 23/046 |
| 9,945,796 | B2 * | 4/2018 | Terashita | G01N 23/223 |
| 2007/0121181 | A1 * | 5/2007 | Moon | G01N 23/2005 359/2 |
| 2008/0144914 | A1 * | 6/2008 | Wagner | A61B 6/0421 382/132 |
| 2009/0066939 | A1 * | 3/2009 | Venkatachalam | G01N 23/04 356/237.1 |
| 2009/0257552 | A1 * | 10/2009 | Warner | G01N 23/046 378/19 |
| 2010/0194749 | A1 * | 8/2010 | Nightingale | G01N 23/046 345/424 |
| 2010/0239068 | A1 * | 9/2010 | Belassel | G01N 3/32 378/72 |
| 2011/0273702 | A1 * | 11/2011 | Jones | G01N 21/8422 356/51 |
| 2011/0299653 | A1 * | 12/2011 | Mishra | G01N 23/02 378/9 |
| 2013/0136225 | A1 * | 5/2013 | Michaels | G01B 15/045 378/4 |
| 2013/0223672 | A1 * | 8/2013 | Smith | G01N 23/087 382/100 |
| 2014/0105368 | A1 * | 4/2014 | Ohara | G01N 23/20008 378/204 |
| 2014/0294136 | A1 * | 10/2014 | Koonankeil | G01N 23/046 378/4 |
| 2016/0274040 | A1 * | 9/2016 | Perez-Willard | G01N 23/2255 |
| 2017/0020481 | A1 * | 1/2017 | Hawker | A61B 6/583 |
| 2018/0001565 | A1 * | 1/2018 | Hocker | B33Y 40/00 |

OTHER PUBLICATIONS

English translation of CN 101435784 (Year: 2009).*
Oct. 20, 2016 Search Report issued in European Patent Application No. 16168887.4.
Oct. 22, 2015 Search Report issued in British Patent Application No. 1508065.8.

\* cited by examiner

METHOD OF SCANNING AEROFOIL BLADES

BACKGROUND

The present invention relates to a method of scanning aerofoil blades, and more particularly relates to a method of CT scanning a plurality of aerofoil blades.

Computed tomography ("CT") is now a widely available technology, and it has been proposed previously to use the CT techniques for investigative work on the internal geometry of aerofoil blades, and in particular turbine blades for gas turbine engines.

Previously proposed methods for CT scanning turbine blades for gas turbine engines have all necessitated scanning a single blade at a time. This is mainly to the extremely high density of material used in the manufacture of most turbine blades (usually high density nickel super-alloys). The extremely high density of the turbine blade material has meant that scanning more than one blade at a time absorbs too much x-ray energy to provide sufficiently clear images of the blades' aerofoil sections for meaningful analysis. This previous requirement to scan each blade individually has thus precluded the use of CT scanning techniques to inspect the internal structure of a large number of blades as would be required, for example, for routine inspection in a production environment. CT scanning has therefore tended to be used on an ad hoc basis for the inspection of small numbers of turbine blades. A convenient and reliable way to scan a plurality of aerofoil blades would therefore offer significant advantages.

It is an object of the present invention to provide an improved method of CT scanning a plurality of aerofoil blades.

SUMMARY

Whilst the invention is described herein with particular reference to CT scanning turbine blades for gas turbine engines, it is to be appreciated that embodiments of the invention could involve the scanning of other forms of aerofoil blades such as, for example, compressor blades or fan blades.

According to the present invention, there is provided a method of CT scanning a plurality of aerofoil blades. The method may include the steps of; providing a rotatable support arranged for rotation about an axis of rotation and within an energy beam; mounting a plurality of aerofoil blades to the support in spaced-apart relationship to one another so as to form at least one array around the axis of rotation; and rotating the support about the axis within the beam; wherein each blade has an aerofoil section and is mounted to the support such that the span of its aerofoil section is substantially parallel to the axis of rotation, wherein the method also involves providing an elongate identification element on the rotatable support, the identification element being arranged such that its longitudinal axis is substantially parallel to the axis of rotation and having a transverse cross-sectional shape along at least part of its length which includes a plurality of different peripheral edge features, each said edge feature corresponding to and being directed towards a respective said blade to thereby facilitate identification of individual said blades in a CT output obtained via the method.

Optionally, said identification element is provided in the form of a pillar fixed to the rotatable support.

Conveniently, said identification element is arranged such that its longitudinal axis is substantially coincident with the axis of rotation of the support such that the blades in the or each said array are arranged around the identification element.

Advantageously, said cross-sectional shape of the identification element is substantially polygonal and has a number of sides equal to the number of aerofoil blades in the or each said array.

Preferably, each said side is arranged in facing relation to a respective said blade.

Conveniently, either all, or all except one, of said sides has a respective said peripheral edge feature formed along its length.

Advantageously, said peripheral edge features include at least one of recesses and projections.

Preferably, said peripheral edge features are configured so as to be visible both on the exterior of the identification element and in said CT output obtained via the method.

Conveniently, at least one of said peripheral edge features is configured such that its cross-sectional shape varies along at least part of the length of the identification element, and wherein the method involves analysing the configuration of the or each said edge feature visible in said CT output to determine the axial position of a CT slice taken through said blades and said identification element.

Advantageously, said identification element is formed of material having a density which is lower than that of the material from which the blades are formed.

Optionally, said identification element is formed from a resin.

Conveniently, said identification element is formed from a polymeric material.

Preferably, the method further involves the provision of a datum element on the rotatable support, the datum element being configured so as have an end surface arranged orthogonal to the axis of rotation and spaced from the support by a predetermined distance.

Advantageously, the method involves taking a datum CT scan in the form of a slice through the blades and orthogonal to the axis of rotation at a position spaced from the support by said predetermined distance such that the end surface of the datum element appears in the resulting CT image, and thereafter taking subsequent CT scans in the form of respective parallel slices through the blades at predetermined offset distances from said datum scan.

Conveniently, said datum element is provided in the form of an elongate post fixed to the rotatable support.

Preferably, said datum post is arranged such that its longitudinal axis is substantially parallel to the axis of rotation of the rotatable support.

Advantageously, said datum post is provided within said array of blades such that said blades are arranged around the datum post.

Conveniently, said datum element is formed from a material having a similar density to the material from which the blades are formed.

Optionally, said datum element is formed from steel.

The method including the steps of: providing a rotatable support arranged for rotation about an axis of rotation and within an energy beam; mounting a plurality of aerofoil blades to the support in spaced-apart relationship to one another so as to form at least one array around the axis of rotation; and rotating the support about the axis within the beam; wherein each blade has an aerofoil section and is mounted to the support such that the span of its aerofoil section is substantially parallel to the axis of rotation, the blades being arranged such that no line orthogonal to the axis of rotation intersects the aerofoil section of more than one blade.

Optionally, said step of mounting a plurality of blades to the support involves forming a plurality of said arrays of blades; the arrays being spaced from one another along the axis of rotation, and each array comprising a plurality of said blades.

Preferably, the blades in the or each said array are substantially identical to one another and are mounted to said support such that the or each said array is rotationally symmetrical about the axis of rotation.

Advantageously, the blades in the or each said array are equi-spaced around the axis.

Conveniently, the blades are mounted to the support such that the chord line of each blade's aerofoil section makes a tangent to a circle centred on the axis of rotation.

Preferably, each blade is mounted to the support such that the leading edge of its aerofoil section is proximal to the axis of rotation, and the trailing edge of its aerofoil section is distal to the axis of rotation.

Alternatively, each blade may be mounted to the support such that the trailing edge of its aerofoil section is proximal to the axis of rotation, and the leading edge of its aerofoil section is distal to the axis of rotation.

Advantageously, the total number of aerofoil blades mounted to the support in the or each array is an odd number.

Optionally, the total number of aerofoil blades mounted to the support in the or each array is three.

Preferably, said step of mounting the blades to the support involves orienting each blade relative to the support via the use of an ancillary alignment tool.

Advantageously, each blade is engaged by said ancillary alignment tool and the tool is then oriented so as to adopt a predetermined position relative to the support, whereupon the blade is releasably fixed to the support and the alignment tool is then disengaged from the blade.

Preferably, said energy beam is an x-ray beam.

BRIEF DESCRIPTION OF THE DRAWINGS

So that the invention may be more readily understood, and so that further features thereof may be appreciated, embodiments of the invention will now be described by way of example with reference to the accompanying drawings in which.

DETAILED DESCRIPTION

Figure 1:
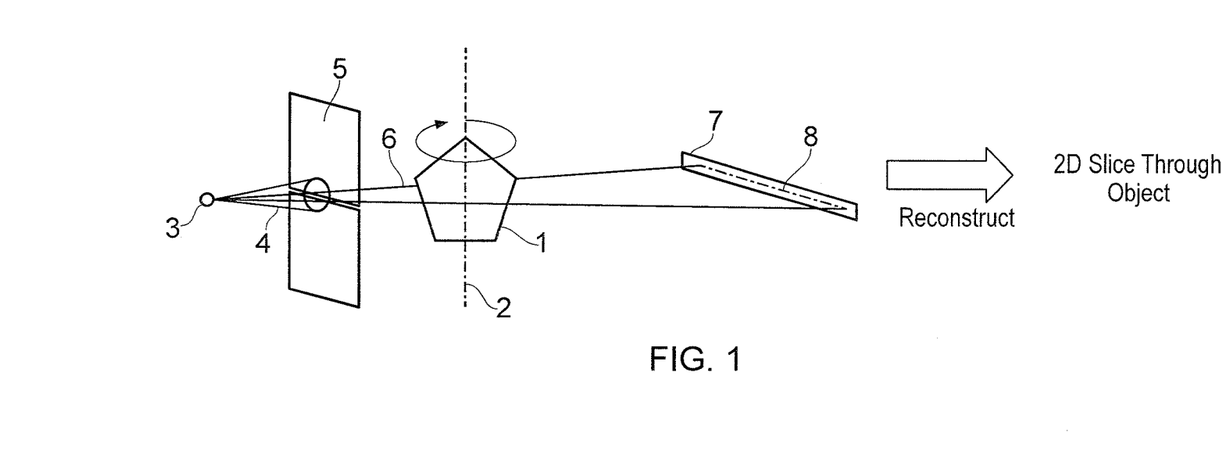
FIG. 1 is a schematic illustration showing an exemplary two-dimensional CT technique.

Turning now to consider the drawings in more detail, FIG. 1 illustrates the basic principles of an exemplary two-dimensional CT scanning technique of a type which may be used in the method of the present invention. A three-dimensional object 1 to be scanned is shown arranged for rotation about an axis of rotation 2. An x-ray source 3 is located to one side of the object 1, and emits a conical x-ray beam 4. A collimator 5 is interposed between the x-ray source 3 and the object 1 and is configured to filter the conical beam 5 of x-rays so that only x-rays travelling in a plane substantially orthogonal to the axis of rotation 2 are permitted to pass through the collimator and thus reach the object 1. A substantially planar fan-shaped beam 6 of x-rays is thus directed towards the object 1, and the object 1 is rotated about its axis 2 through at least 360° within the fan shaped beam 6. An x-ray detector 7 is placed behind the object 2, and receives and detects x-rays reaching it from the object 2, thereby producing a one-dimensional output 8. The output 8 from the detector 7 may then be reconstructed and processed in a manner known per se to produce a two-dimensional image in the form of a slice taken through the object 1 in the plane of the fan-shaped beam 6. By adjusting the relative positions of the object 1 and the fan-shaped beam 6 and repeating the process, a plurality of slices can be taken through the object 1 at different positions along its axis 2.

As will be appreciated, in order to capture complete slices through the object 1 via the type of technique described above, it is important that the object 1 should remain entirely within the x-ray beam 6 whilst it is rotated. However, in order to ensure a high degree of resolution in the resulting CT images that are obtained, the object should be placed as close as possible to the x-ray source 3 in order to ensure that the x-rays which are incident on the object are at the highest possible power.

Turbine blades for gas turbine engines are typically of a sufficiently small size to allow them to be scanned individually with good results via the type of technique described above. The small size of individual blades allows them to be located close to the x-ray source, thereby providing CT images of good resolution. However, in order to scan a plurality of such blades simultaneously it is necessary to arranged the blades in an array, and then to rotate the entire array within the x-ray beam 6. As will be appreciated, an array of blades will inevitably be larger than an individual blade and so such an array cannot be located as close to the x-ray source 3, which means that it has not previously been possible to scan a plurality of blades simultaneously with sufficiently high resolution in the obtained images.

Another problem which the inventors have identified when trying to scan a plurality of blades arranged in an array simultaneously arises from the fact that turbine blades for gas turbine engines are generally formed of extremely dense material (e.g. nickel superalloys). The very high density of the blade material absorbs a large amount of x-ray energy which can also reduce the resolution of the resulting CT images. This problem can be exacerbated when trying to scan a plurality of blades simultaneously because individual blades within the array can become overlapped and thus some spend time within the x-ray "shadow" of others as the array as a whole is rotated within the x-ray beam 6.

Whilst it is envisaged that the methods of the present invention will be particularly suited to use with a two-dimensional CT scanning technique of the type illustrated in FIG. 1 and described above, it is also possible to use the methods with three-dimensional CT scanning techniques. For the sake of completeness, FIG. 2 therefore illustrates the basic principles of an exemplary three-dimensional CT scanning technique of a type which may be used in the method of the present invention.

Figure 2:
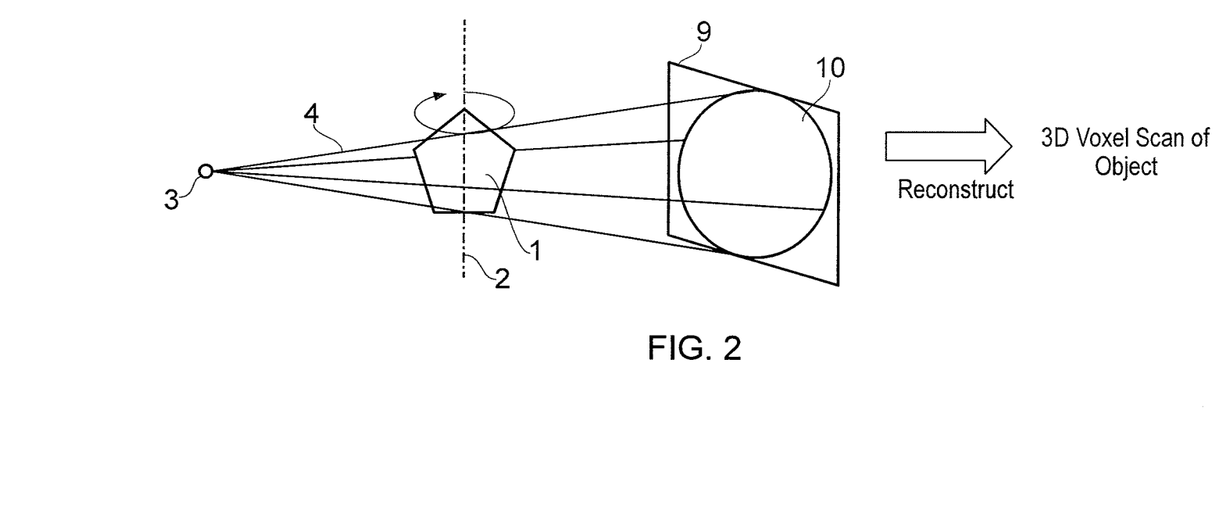
FIG. 2 is a schematic illustration similar to that of FIG. 1, but which shows an exemplary three-dimensional CT technique.

The object 1 to be scanned is again arranged for rotation about an axis of rotation 2. An x-ray source 3 is located to one side of the object 1, and emits a conical x-ray beam 4. In this arrangement, however, there is no collimator 5 between the x-ray source 3 and the object 1, and so the object 1 is rotated about its axis 2 within the conical x-ray beam 6. A flat panel x-ray detector 9 is placed behind the object 2, and receives and detects x-rays reaching it from the object 2, thereby producing a two-dimensional output 10. The output 10 from the detector 9 may then be reconstructed and processed in a manner known per se to produce a three-dimensional voxel scan of the object 2.

Figure 3:
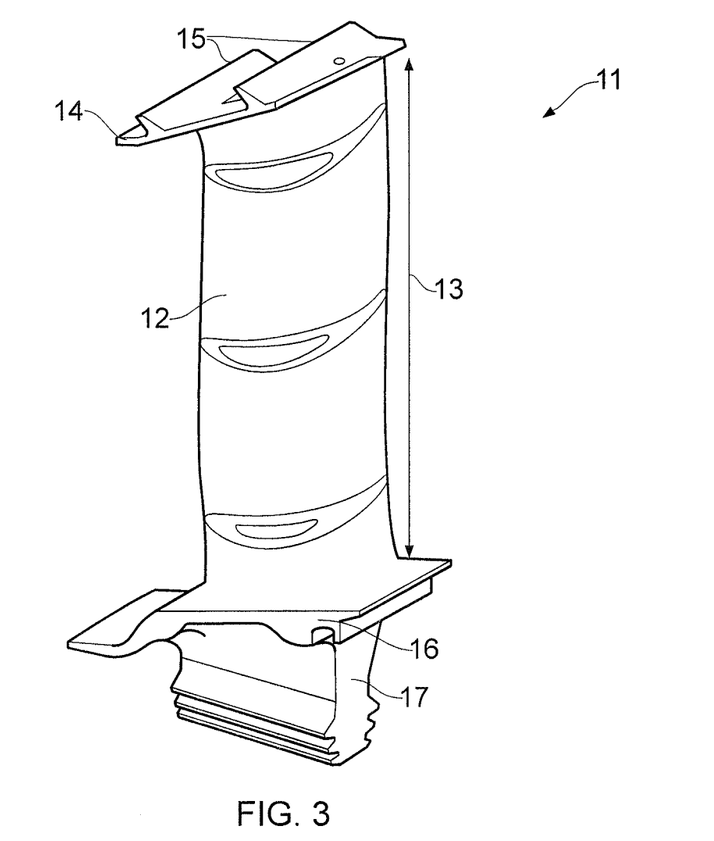
FIG. 3 is a perspective view showing a turbine blade for a gas turbine engine, of type which may be CT scanned via the method of the present invention.
Figure 4:
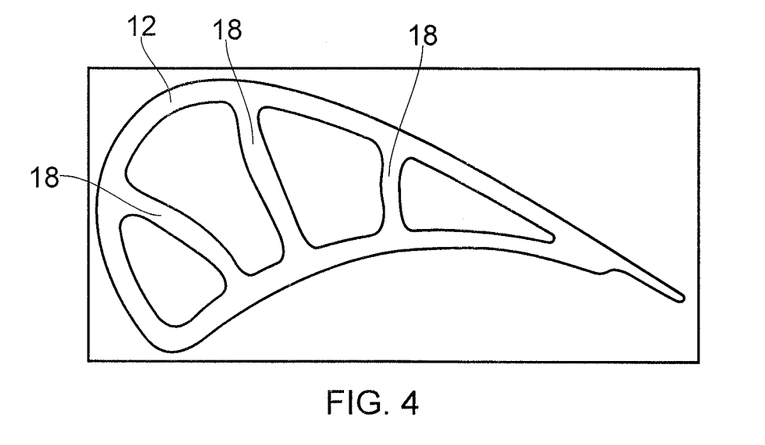
FIG. 4 shows a transverse CT image taken as a slice through an aerofoil section of a turbine blade, so as to show the internal structure of the blade.

FIG. 3 illustrates an exemplary turbine blade of a type which may be scanned via the method of the present invention. As will be appreciated by those of skill in the art, the blade 11 comprises an elongate aerofoil section 12 having a span 13. At one end of the aerofoil section 12 the blade comprises a shroud 14 which may have one or more tip fins 15. At the opposite end of the aerofoil section 12 there is defined a platform 16 and a root portion 17 for use in attaching the blade 11 to the rotor of a turbine. The aerofoil section 12 is generally of primary interest when CT scanning turbine blades, and in particular the internal structure of the aerofoil section 12. FIG. 4 illustrates an exemplary CT image taken as a transverse slice, orthogonal to the span 13, through the aerofoil section 12 of a blade 11. As will be noted, the internal structure of the aerofoil section is generally hollow and comprises a series of reinforcing webs 18.

Turning now to consider FIG. 5, there is illustrated a support 19 which, as will be described in more detail below, is configured to receive and support a plurality of blades 11 of the general type described above. The support 19 comprises a generally planar platform 20, and is configured to be rotatable about an axis of rotation 21 which is orthogonal to the platform 20. A plurality of upwardly open sockets 22 are fixed to the platform 20, and are arranged in an equi-spaced array around the axis of rotation 21. As will be noted, the positions of the sockets 22 are thus rotationally symmetrical about the axis 21. The sockets 22 are each configured to receive a respective turbine blade 11, as will be described below, and in the particular arrangement illustrated there are three such sockets such that the rotatable support 19 is configured to receive and support three turbine blades 11.

The rotatable support 19 also includes an elongate identification element 23 in the form of a pillar mounted to the platform 20 so as to be upstanding therefrom and which is arranged such that its longitudinal axis is substantially coincident with the axis of rotation 21 of the support 19. Adjacent the identification element 23, there is provided a shorter datum element 24 which is also elongate in form and is mounted to the platform 20 so to be upstanding therefrom. The datum element is arranged such that its longitudinal axis is substantially parallel to the axis of rotation 21 of the support 19. Further details of the identification element 23 and the datum element 24, and their respective functions in the method of the present invention, will be described hereinbelow.

Figure 6:
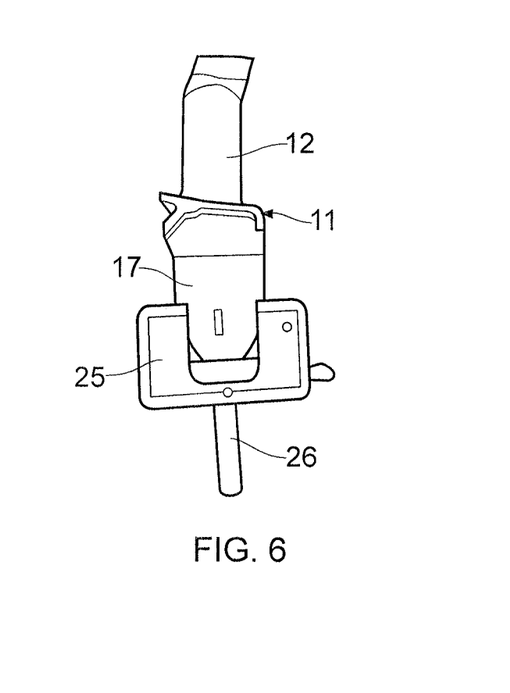
FIG. 6 is a perspective view showing a turbine blade engaged by a clamp for attachment to the rotatable support of FIG. 5.

The turbine blades 11 are mounted to the rotatable support 19 such that the spans of their respective aerofoil sections 12 are substantially parallel to the axis of rotation 21 of the support 19. This is achieved by securely fitting a support clamp 25 to the root portion 17 of each blade 11, as illustrated in FIG. 6. As will be noted, each clamp 25 is securely engaged around the root portion 17 of a respective blade 11 at a position spaced below the platform 16, and hence in spaced relation to the aerofoil section 12, of the blade 11. Each clamp 25 has an elongate mounting pin 26 which is sized and configured to be received within a respective mounting socket 22 on the rotatable support 19, whereupon the socket 22 is tightened around the pin 26 to engage the pin tightly, thereby fixing the blade in position on the support 19. However, it is important to orientate the blades 11 carefully with respect to the support 19, both in terms of the height of the blades 11 above the platform 20, and also in terms of the rotational position of the blades relative to their respective mounting sockets 22.

Figure 7:
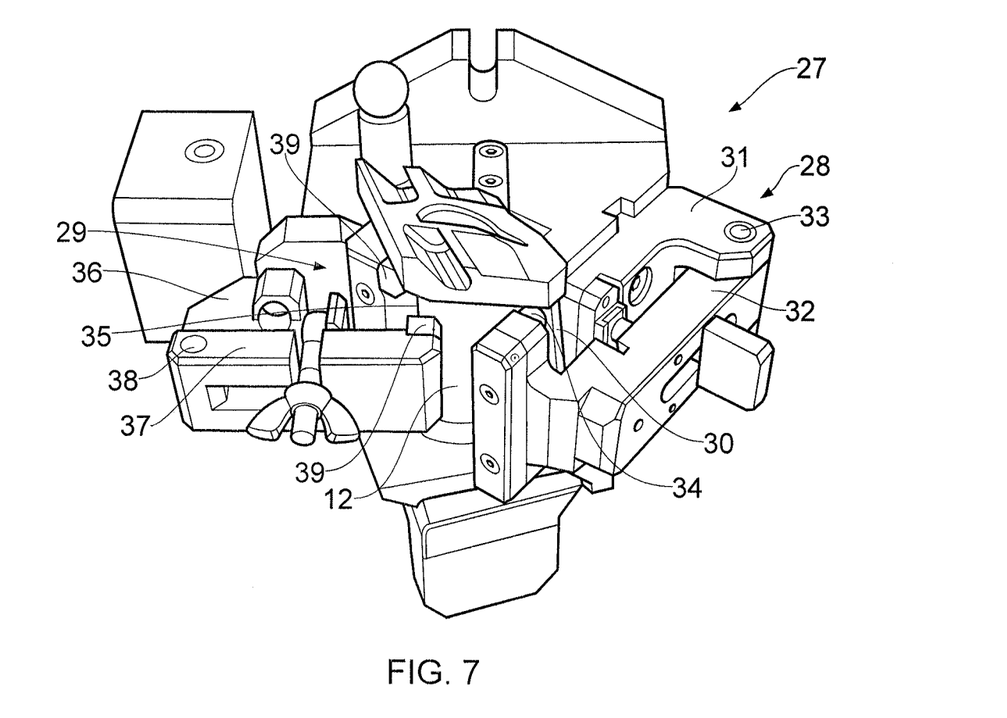
FIG. 7 shows an alignment tool engaged with a turbine blade.

FIG. 7 illustrates part of an ancillary alignment tool 27 which is used to orientate and properly align the blades 11 relative to one another and the rotatable support 19 when they are each engaged with their respective sockets 22. The alignment tool 27 includes a pair of clamps 28, 29, each of which is configured to clampingly engage part of the aerofoil section 12 of each blade 11 in turn. FIG. 7 shows the blade 12 absent its mounting clamp 25 for the sake of clarity.

Figure 8:
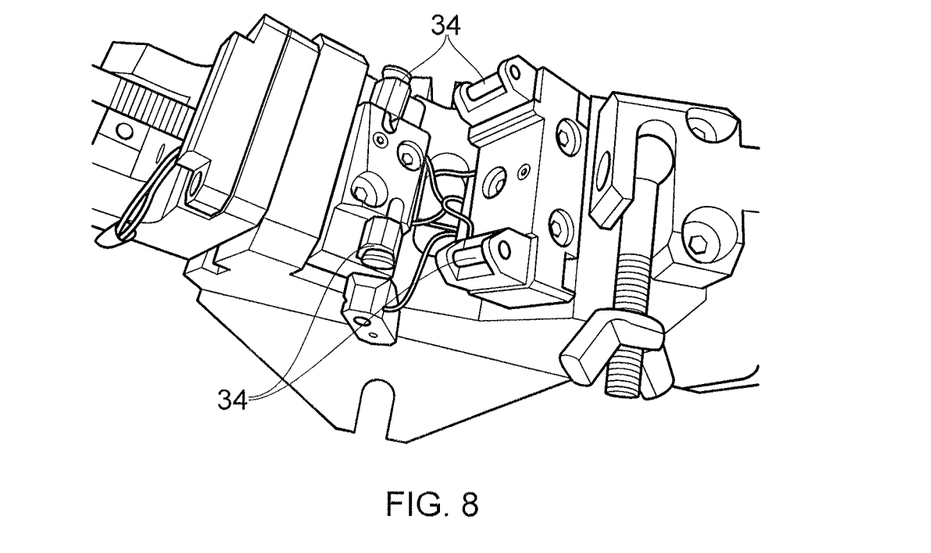
FIG. 8 shows a first clamp forming part of the alignment tool of FIG. 7, the clamp being shown in an open configuration.

One of the two clamps 28 of the alignment tool 27 is configured to engage the aerofoil section 12 of the blade around the trailing edge 30 of the aerofoil section, and comprises a pair of clamp members 31, 32 which are pivotally connected to one another at 33. The clamping members 31, 32 of the clamp 28 are tightly closed around the trailing edge 30 of the aerofoil section 12, such that electrodes 34 (shown most clearly in FIG. 8 which shows the clamp 28 in an open configuration) on the clamping members 31, 32 engage and make contact with the surface of the aerofoil section 12.

Figure 9:
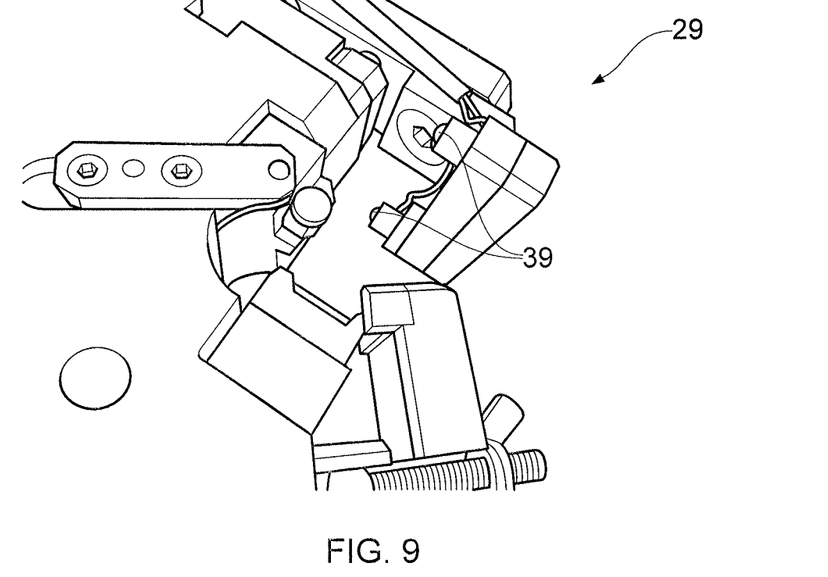
FIG. 9 shows a second clamp forming another part of the alignment tool, the clamp again being shown in an open configuration.

Similarly, the other clamp 29 of the alignment tool 27 is configured to engage the aerofoil section 12 of the blade 11 around its leading edge 35, and also comprises a pair of clamp members 36, 37 which are pivotally connected to one another at 38. The clamping members 36, 37 of the clamp 29 are tightly closed around the leading edge 35 of the aerofoil section 12, such that electrodes 39 (shown most clearly in FIG. 9 which shows the clamp 29 in an open configuration) on the clamping members 36, 37 engage and make contact with the surface of the aerofoil section 12.

Figure 10:
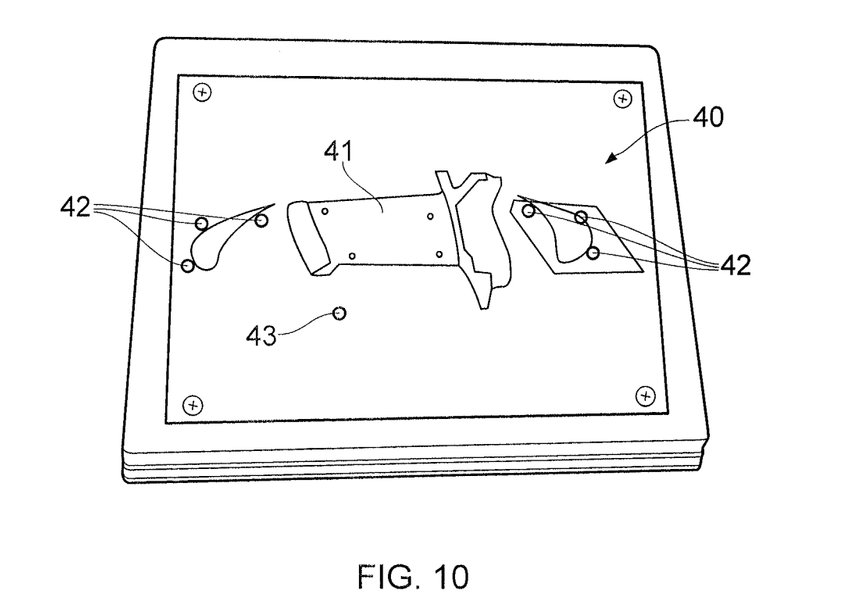
FIG. 10 shows a display panel which may be used to confirm accurate engagement of the alignment tool with the turbine blade.

The electrodes 34, 39 on the two clamps 28, 29 of the alignment tool 27 are connected to a display panel 40 which is shown in 10 and comprises a graphical representation 41 of the blade 11. The display panel has a series of lights 42 or other indicia, each of which corresponds to a respective electrode 34, 39 and which is illuminated when the respective electrode makes contact with the surface of the blade's aerofoil section 12. The display panel 40 may also include an additional indicator light 43, or other indicia, which becomes illuminated when both of the clamps 28, 29 of the alignment tool 27 are tightly closed and all of the electrodes 34, 39 are in contact with the surface of the aerofoil section, thereby providing convenient visual confirmation of proper engagement of the tool 27 with the blade 11.

As will therefore be appreciated, the above-described tool arrangement, comprising clamps 28, 29 and electrodes 24, 39 is configured to engage the aerofoil section of each blade in turn in a very precise and repeatable manner, thereby ensuring accurate orientation of the tool relative to the blade 11.

Figure 11:
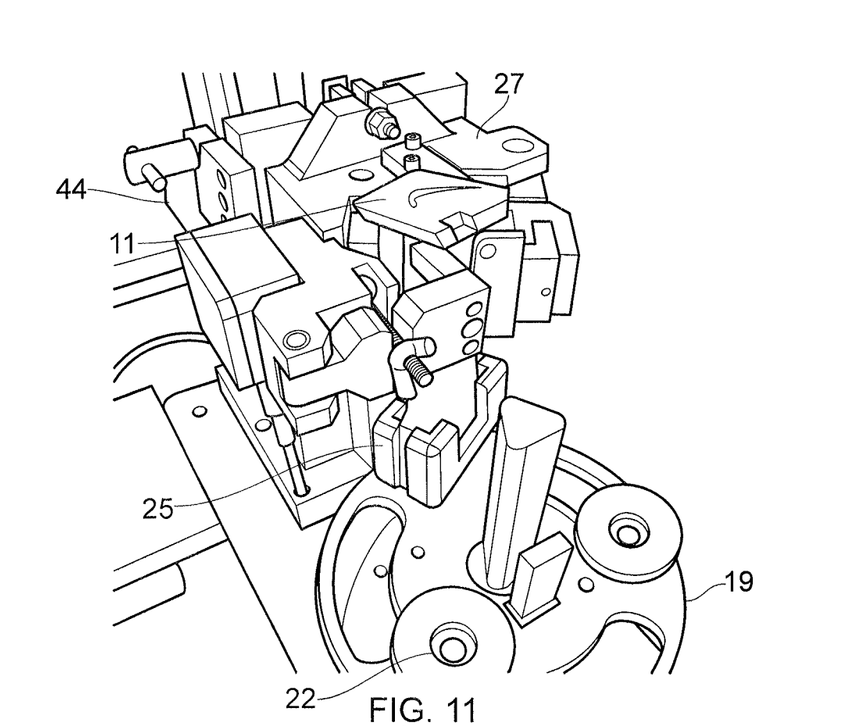
FIG. 11 is a perspective view showing the alignment tool being used to align a turbine blade with respect to the rotatable support.

Turning now to consider FIG. 11, the alignment tool 27 is shown engaged with a turbine blade 11 in the manner described above. Also shown is a mounting clamp 25 engaged with the root portion 17 of the blade 11, at a position below the aerofoil section 12 of the blade and thus also below the alignment tool 27. The alignment tool 27 may be mounted to, and controlled by, a three-axis manipulator arrangement 44 which may then be used to move the alignment tool 27 so as to position the mounting pin 26 of the mounting clamp 25 affixed to the blade 11 above a respective mounting socket 22 on the rotatable support 19. The mounting pin 26 is then lowered into the socket to a predetermined depth, and the alignment tool 27 is carefully manipulated to position the blade 11 accurately relative to the rotational support 29, both in terms of its height above the platform 20 and in terms of its rotational position relative to the socket 22. When the blade 11 is properly positioned (as will be described in more detail below), the socket 22 is tightened around the mounting pin 26, and the alignment tool 27 is then removed from the blade 11 to leave the blade mounted in position on the rotatable support with the span 13 of its aerofoil section 12 lying parallel to the rotational axis 21 of the support 19. The alignment tool 27 can then be engaged with another blade 11 and used to align and mount the next blade to the support 19. The process is repeated until a respective blade 11 is mounted to each mounting socket 22.

Figure 12:
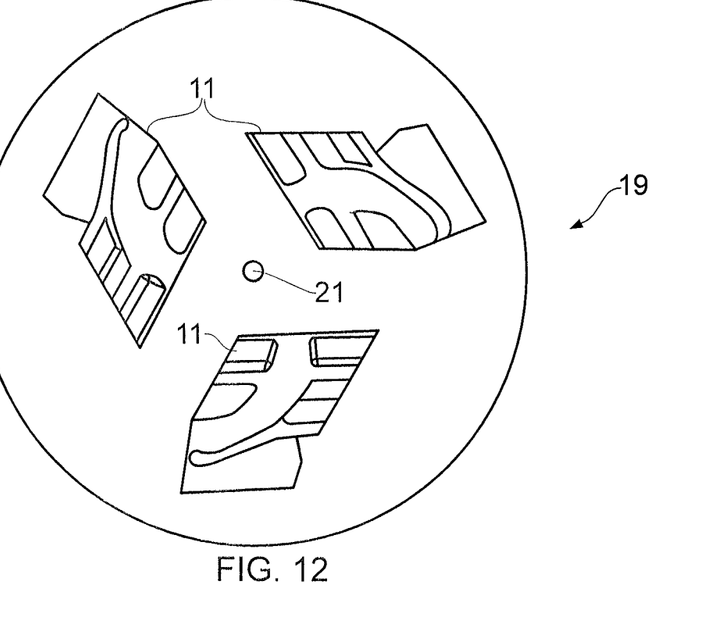
FIG. 12 is a schematic plan view, from above, showing a plurality of turbine blades mounted to the rotatable support and aligned with respect thereto.

FIG. 12 is a schematic plan view, from above, showing three turbine blades 11 mounted to the rotatable support 19 in a favoured orientation relative to one another and to the support 19. As will be appreciated, the blades 11 are mounted in equi-spaced relationship to one another so as to form an array around the axis of rotation 21 of the support 19. Also, it is to be noted that the span 13 of each blade's aerofoil section 12 is substantially parallel to the axis of rotation 21. Because the blades 11 are preferably identical to one another, the resulting array of blades is thus rotationally symmetrical about the axis of rotation 21.

As will be appreciated, when the blades 11 are mounted to the rotatable support 20 as described above, the support 20 will be rotated about its axis 21 such that the array of blades 11 will rotate as a whole around the axis 21 within the x-ray beam 6, in the manner described above with reference to FIG. 1. In this manner, a plurality of blades 11 can be CT scanned simultaneously such that a plurality of slices can be taken through the aerofoil sections 12 of all of the blades 11 together. However, in order to ensure that the array of blades 11 can be located as close as possible to the x-ray source 3 in order to make optimum use of the x-ray energy, whilst ensuring that the aerofoil sections 12 of all of the blades 11 remain within the x-ray beam 6 at all times, it is important to ensure that the blades 11 are located as close as possible to the axis of rotation 21 in order to minimize the overall diameter of the blade array. However, this requirement must be balanced with an additional requirement that at no point during rotation of the blade array within the beam 6 should the aerofoil section 12 of any of the blades be "hidden" from the x-ray source 3 by falling into the "shadow" of another blade 11, because if that were to happen then the amount of dense material through which the x-rays must pass would increase significantly, thereby reducing resolution in the images obtained.

Figure 13:
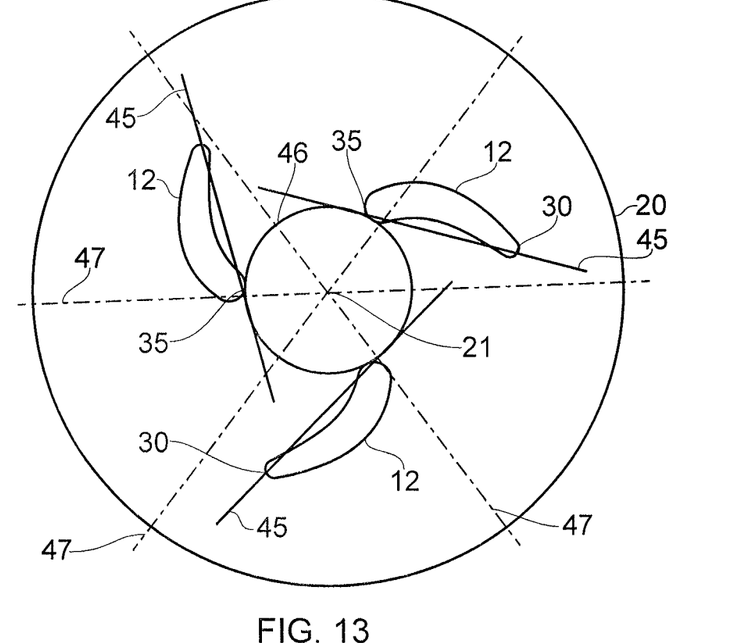
FIG. 13 is a view similar to that of FIG. 12, but which shows a transverse cross-section through the aerofoil sections of the blades to show the manner in which the blades may be oriented with respect to one another and the rotatable support.

FIG. 13 is a transverse cross-sectional representation through the aerofoil sections 12 of the array of blades 11 mounted to the rotatable support 19 in a preferred arrangement. The above-described use of the alignment tool 27 is intended to ensure accurate positioning of the blades 11 in this orientation.

As will be noted, the blades 11 shown in an arrangement in which their leading edges 35 are proximal to the axis of rotation 21 and their trailing edges 30 are distal to the axis of rotation 21. However it is envisaged that in other embodiments the reverse orientation could be employed such that the blades' trailing edges 30 would be proximal to the axis of rotation 21 and their leading edges 35 would be distal to the axis of rotation. Regardless of which of these orientations is used, however, it is proposed that the blades 11 will be arranged such that the chord line 45 of each aerofoil section 12 will make a tangent to a notional circle 46 centred on the axis of rotation 21. As will be appreciated, the diameter of this notional circle 46 should be as small as possible of the reasons already mentioned above. Nevertheless, in order to prevent overlap of the aerofoil sections 12 of respective blades within the x-ray beam 6, it is proposed that the blades 11 will all be arranged, both in terms of number and their radial position from the axis of rotation 21, such that no notional line 47 can be constructed orthogonal to the axis of rotation (i.e. in the plane of FIG. 13) which would intersect the aerofoil section 12 of more than one blade 11. A number of such notional lines 47 are shown in FIG. 13 in phantom, and it will be noted that all intersect only the aerofoil section 12 of a single blade 11. It is proposed that the blades 11 will be located as closely as possible to the rotational axis 21 whilst still preserving this characteristic.

As will be appreciated, the above-described positioning requirements of the blades 11 can most conveniently be achieved when the total number of blades 11 in the array around the axis of rotation 21 is an odd number. By using an array of three blades in particular, the overall diameter of the resulting array can be minimized and so three is presently considered to represent the optimum number of blades 11. Nevertheless, it is proposed that in some embodiments, a number of discrete arrays of blades with the above-described properties could be arranged in spaced-apart relation along the axis of rotation 21, (for example by providing the support 19 with a plurality of spaced apart platforms 19 with associated mounting sockets 22) thereby permitting a larger number of blades 11 to be mounted onto the rotatable support 19 at a time without adversely affecting the CT scanning performance of the arrangement.

As will be appreciated, when Ct scanning a plurality of blades 11 simultaneously as proposed above, the resulting images taken as slices through the aerofoil sections 12 of the blades 11 will feature all of the blades 11 in the array supported by the rotatable support 19. It is therefore important to provide a way to identify individual blades 11 within the array, both in the resulting CT images and also visually on the rotatable support 19. This is the function of the identification pillar 23.

Figure 14:
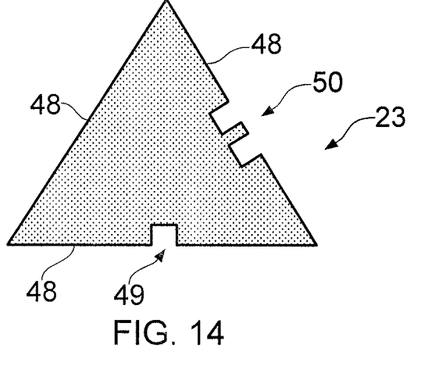
FIG. 14 is a transverse cross-sectional view through an identification element provided on the rotatable support.

As indicated above, in preferred arrangements the identification pillar 23 is elongate and arranged such that its longitudinal axis is substantially coincident with the rotational axis 21 of the rotatable support 19. Accordingly, it will be noted that the identification pillar 23 is located within the array of blades 11 such that the blades 11 are distributed around the identification pillar 23. FIG. 14 illustrates a transverse cross-sectional view taken through the identification pillar 23 at a height above the platform 20 of the rotatable support which corresponds to a position through the aerofoil sections 12 of the blades 11. As will be noted, the illustrated pillar 23 has a triangular shape in cross-section and thus has three straight side edges 48, each of which of course corresponds to a respective planar side face of the pillar. It is proposed that the pillar 23 will be oriented such that each side 48 will be arranged in facing relation to a respective blade 11 mounted to the rotatable support 19 in the manner described above.

As also illustrated in FIG. 14, one of the side edges 48 of the pillar 23 is entirely straight, but the other two are provided with respective peripheral edge features 49, 50 which are thus also directed towards respective blades 11 mounted to the rotatable support 19. The edge features 49, 50 are both provided in the form of recesses, but each has a different form. For example, in the arrangement illustrated one of the edge features 49 is provided in the form of a single square-sectioned recessed groove extending up at least part of the axial length of the pillar 23, whilst the other edge feature 50 is provided in the form of two spaced-apart square-sectioned recessed grooves extending up at least part of the axial length of the pillar 23. As will therefore be appreciated, in transverse cross-section as illustrated in FIG. 14, the edge feature 49 appears as a single square recess, whilst the other edge feature 50 appears as a pair of square recesses.

It is proposed that the identification pillar will be made from a material which is considerably less dense than the material from which the turbine blades 11 are made, so that the pillar 23 will not absorb as much x-ray energy as the blades 11 during the CT scanning process, thereby ensuring that the CT output obtained will still have good resolution properties. Nevertheless, it is important that the transverse cross-sectional shape of the pillar 23 will feature in the CT output so that it the different shape configurations of each of its faces can be used to facilitate identification of individual said blades in the CT output. It is therefore currently proposed that the pillar 23 will be formed from a resin or polymeric material.

As well as the above-described peripheral edge features 49, 50 being configured to appear in the CT output images, it is also to be noted that the features 49, 50 will also be visible by the naked eye on the exterior of the identification pillar 23, so that the individual blades 11 in the array mounted to the rotatable support 19 can be identified by the features as they are mounted to the support 19, and both during and after the CT scanning process.

Figure 15:
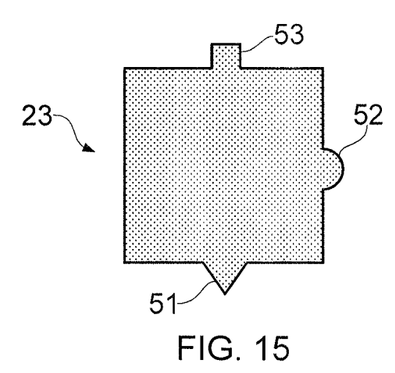
FIG. 15 is a transverse cross-sectional view similar to that of FIG. 14, but which is taken through an alternative configuration of identification element.
Figure 16:
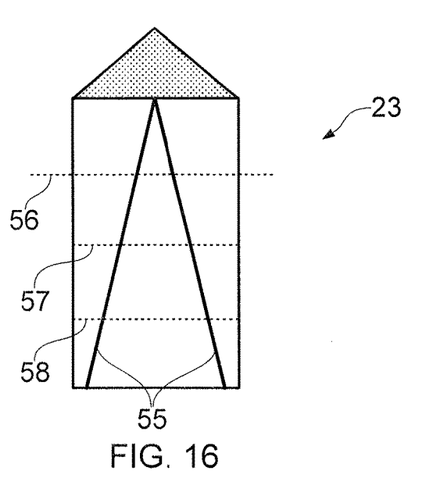
FIG. 16 is a schematic side elevational view of an another alternative configuration of identification element.
Figure 17:
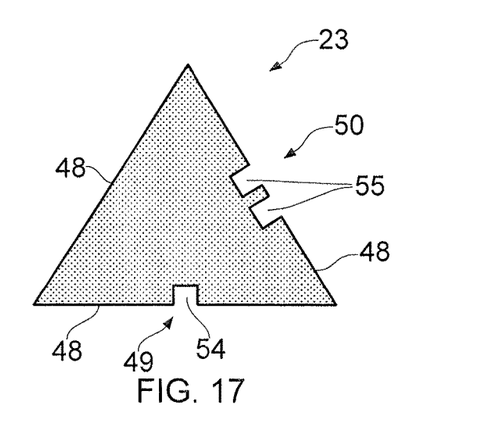
FIG. 17 is a transverse cross-sectional view through the identification element of FIG. 16 at a first longitudinal position.

FIG. 15 illustrates a transverse cross-sectional view taken through another form of identification pillar 23. As will be noted, in this arrangement the pillar 23 has a square cross-section rather than a triangular one as in the arrangement shown in FIG. 14. The pillar 23 shown in FIG. 15 is thus configured to be used to identify individual blades 11 provided in an array of four such blades arranged around the pillar 23, such that each side edge of the square cross-sectional shape, and thus each planar side face of the pillar 23, is directed towards a respective said blade 11. Furthermore, the pillar 23 illustrated in FIG. 15 has peripheral edge features 51, 52, 53 (along all except one of its side edges) which are each provided in the form of a projection. As will be appreciated, the projections may be provided in the form out outwardly projecting ribs provided along at least part of the axial length of the pillar 23. Each projection 51, 52, 53 is configured so as to have a different cross-sectional shape, and so the arrangement illustrated in FIG. 15 includes a projection 51 of triangular configuration in cross-section, a projection 52 of semi-circular configuration in cross-section, and a projection 53 of square configuration in cross-section. Each side of the pillar 23 thus has an edge profile which is visually different from the other sides.

It is often important to ensure that CT slices through the aerofoil sections 12 of the blades 11 are taken at specific positions along the span 13 of the aerofoil sections 12, and thus at specific heights above the platform 20 of the rotatable support 19. The edge features of the identification pillar 23 can therefore be specially configured so that the cross-sectional images taken through the pillar 23 via the CT process can be used accurately to determine the respective corresponding positions along the spans 13 of the aerofoil sections 12. FIGS. 16 to 19 illustrate an example of an identification pillar 23 configured for this purpose.

Figure 5:
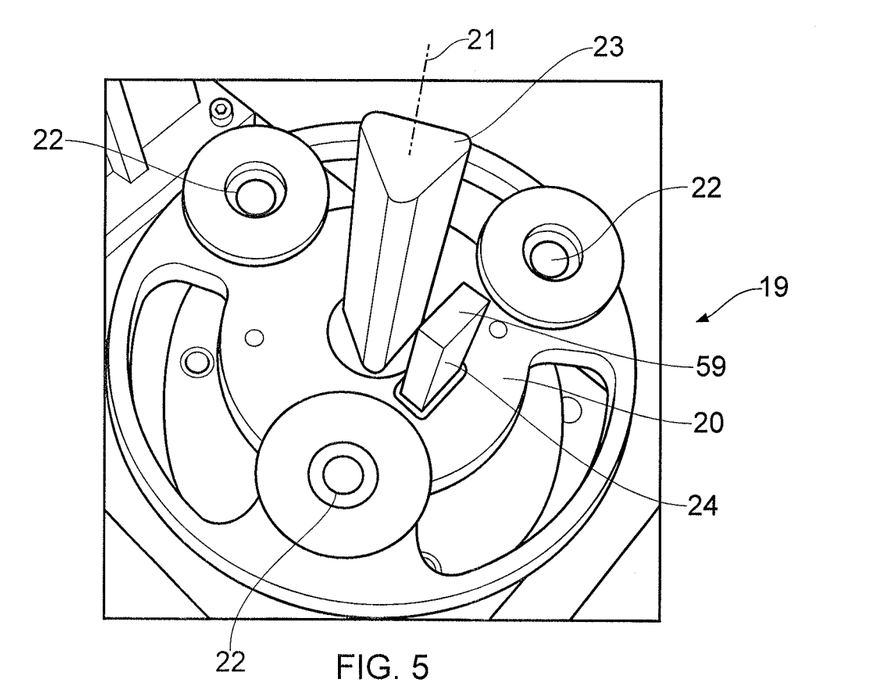
FIG. 5 is perspective view, from above, of a rotatable support which can be used in the method of the present invention to support a plurality of blades for CT scanning.

The pillar 23 illustrated in FIGS. 16 to 19 can be considered to be similar in many respects to the triangular sectioned pillar 23 illustrated in FIGS. 5 and 14 and described above. For example, as will be noted from FIG. 17 in particular, it will be noted that one side 48 of the pillar is provided without any edge feature, another side 48 is provided with an edge feature 49 in the form of a single square-sectioned recessed groove 54, and another side 48 is provided with an edge feature 50 in the form of two spaced-apart square-sectioned recessed grooves 55. However, in this arrangements the two spaced-apart grooves 55 are not parallel to one another along the length of the pillar 23, but are instead arranged such that they converge towards one another with increasing distance along the axis of the pillar 23 above the rotatable support 19. This is illustrated most clearly in FIG. 16, where the converging relationship of the two grooves 55 is shown as viewed from the side of the pillar 23.

Figure 18:
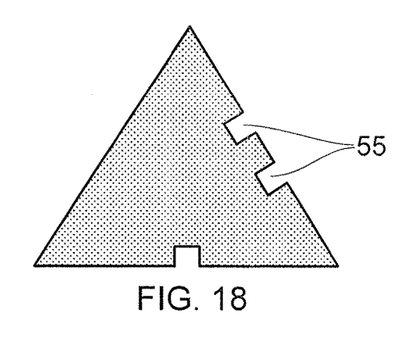
FIG. 18 is a transverse cross-sectional view through the identification element of FIGS. 16 and 17 at a second longitudinal position.
Figure 19:
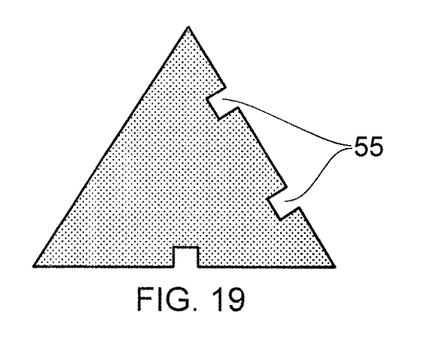
FIG. 19 is a transverse cross-sectional view through the identification element of FIGS. 16 to 18 at a third longitudinal position.

As will therefore be appreciated, the relative spacing between the grooves 55 as viewed in transverse cross-section through the pillar 23, and thus in the CT slices taken through the pillar 23 and the blades 11 during the scanning process can be used to determine the axial position of each CT slice through the blades 11. As will therefore be appreciated, FIG. 17 denotes the cross-sectional shape of the pillar at a first axial position 56 indicated in FIG. 16, and are the grooves 55 are thus relatively close to one another. FIG. 18 denotes the cross-sectional shape of the pillar 23 at a second axial position 57, which is lower than the first position 56 and so the grooves 55 can be seen to be spaced further apart at this position. FIG. 19 denotes the cross-sectional shape of the pillar 23 at a third axial position 58, which is lower than the second position 57, and so the grooves 55 can be seen to be spaced even further apart at this position. Of course, this characteristic of the pillar 23 can be embodied in projecting ribs instead of grooves.

The datum element 24 is intended to be used to determine a datum height above the platform 20 of the rotatable support 19. Accordingly, the datum element 24 is configured to have a planar end surface 59 which is oriented so as to be substantially orthogonal to the axis of rotation 21 of the rotatable support, and which is spaced above the platform 20 of the rotatable support 19 by a predetermined distance. The datum element 24 is preferably made from machinable material having a density which is generally comparable to that of the turbine blades 11 to be inspected. It is therefore proposed that the datum element may be formed from tool steel.

The predetermined height at which the end surface 59 of the datum element is spaced above the platform 20 is preferably set such that it is below the aerofoil sections 12 of the blades 11 which are of most interest, and so the datum element will not appear in CT slices which are taken through the aerofoil sections 12. Nevertheless, the datum element 24 can be used to determine the vertical height above the platform 20 for a datum CT slice which can be captured initially and which can then be used as a reference to accurately determine the vertical height of subsequent CT slices which may then be taken through the aerofoil sections 12 at predetermined offset distances from the datum slice. The datum CT slice will be taken at a position along the axis of rotation 21, and thus above the platform 20, such that the end surface 59 of the datum element 24 appears in the resulting output image.

Whilst the invention has been described above with specific reference to use in scanning turbine blades for gas turbine engines, it is to be appreciated that the invention could also be used to scan other types of aerofoil blades such as, for example, compressor blades.

When used in this specification and claims, the terms "comprises" and "comprising" and variations thereof mean that the specified features, steps or integers are included. The terms are not to be interpreted to exclude the presence of other features, steps or integers.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. An apparatus for CT scanning a plurality of aerofoil blades, the apparatus comprising:
    a rotatable support arranged for rotation about an axis of rotation and within an energy beam, the rotatable support including a plurality of mount locations in a spaced-apart relationship to one another so as to form at least one array around the axis of rotation, each of the plurality of mount locations being configured to receive one of a plurality of aerofoil blades, wherein each of the plurality of aerofoil blades has an aerofoil section such that, when mounted to the support at respective ones of the plurality of mount locations, a span of an aerofoil section of each of the plurality of aerofoil blades is substantially parallel to the axis of rotation; and
    an elongate identification element on the rotatable support, the identification element being arranged such that a longitudinal axis of the identification element is substantially parallel to the axis of rotation of the rotatable support, the identification element having a transverse cross-sectional shape along at least part of a length of the identification element which includes a plurality of edges, each of the plurality of edges of the transverse cross-sectional shape being directed towards a respective one of the plurality of mount locations, and each of the plurality of edges of the transverse cross-sectional shape having a different peripheral edge configuration to thereby facilitate identification of individual ones of the plurality of aerofoil blades mounted at the respective ones of the plurality of mount locations in a CT output.

2. The apparatus according to claim 1, wherein said identification element is provided in a form of a pillar fixed to the rotatable support.

3. The apparatus according to claim 1, wherein said peripheral edge features include at least one of recesses and projections.

4. The apparatus according to claim 1, wherein said identification element is formed of material having a density which is lower than that of the material from which the blades are formed.

5. The apparatus according to claim 1, further comprising a datum element provided on the rotatable support, the datum element being configured so as have an end surface arranged orthogonal to the axis of rotation and spaced from the support by a predetermined distance, such that the end surface of the datum element will appear in a CT image to provide a datum scan, and subsequent CT scans can be made in the form of respective parallel slices through the mount locations at predetermined offset distances from said datum scan.

6. The apparatus according to claim 2, wherein said identification element is arranged such that its longitudinal axis is substantially coincident with the axis of rotation of the support such that the mount locations of each said array are arranged around the identification element.

7. The apparatus according to claim 6, wherein said cross-sectional shape of the identification element is substantially polygonal and has a number of sides equal to the number of aerofoil blades in each said array.

8. The apparatus according to claim 7, wherein each said side is arranged in facing relation to a respective said mount location.

9. The apparatus according to claim 7, wherein either all, or all except one, of said sides have a respective said peripheral edge feature formed along its length.

10. The apparatus according to claim 3, wherein said peripheral edge features are configured so as to be visible both on an exterior of the identification element and in a CT scan.

11. The apparatus according to claim 3, wherein at least one of said peripheral edge features is configured such that its cross-sectional shape varies along at least part of the length of the identification element, so that an analysis of the configuration of each said edge feature visible in a CT output can determine the axial position of a CT slice taken through said blades and said identification element.

12. The apparatus according to claim 4, wherein said identification element is formed from a resin.

13. The apparatus according to claim 4, wherein said identification element is formed from a polymeric material.

14. The apparatus according to claim 5, wherein said datum element is provided in a form of an elongate post fixed to the rotatable support.

15. The apparatus according to claim 5, wherein said datum element is formed from a material having a similar density to the material from which the blades are formed.

16. The apparatus according to claim 14, wherein said datum post is arranged such that its longitudinal axis is substantially parallel to the axis of rotation of the rotatable support.

17. The apparatus according to claim 16, wherein said datum post is provided within said mount locations such that said mount locations are arranged around the datum post.

* * * * *